United States Patent [19] [11] 4,401,432
Schwartz [45] Aug. 30, 1983

[54] STORAGE, MIXING AND FILTERING RECEPTACLE FOR SYRINGE

[76] Inventor: Boris Schwartz, 625 Lafayette Ave., Hawthorne, N.J. 07506

[21] Appl. No.: 382,290

[22] Filed: May 26, 1982

[51] Int. Cl.³ ..... A61M 5/00
[52] U.S. Cl. ..... 604/89; 604/190
[58] Field of Search ..... 604/87, 88, 89, 90, 604/91, 190, 82, 187, 200-206

[56] References Cited

U.S. PATENT DOCUMENTS

| | | | |
|---|---|---|---|
| 1,744,893 | 1/1930 | Hein | 604/190 |
| 2,907,329 | 10/1959 | Cohen | 604/89 |
| 3,610,297 | 10/1971 | Raaf et al. | 604/89 |
| 4,060,082 | 11/1977 | Lindberg et al. | 604/89 |
| 4,306,554 | 12/1981 | Schwartz et al. | 604/190 |

*Primary Examiner*—John D. Yasko
*Attorney, Agent, or Firm*—Ralph R. Roberts

[57] ABSTRACT

This invention pertains to an add-on device used with a conventional syringe having an outer barrel with a hollow needle mounted thereon. A tubular sheath has a first end slidably and removably mounted on this barrel with a second end retaining a flexible cap portion. Within this flexible cap end, two ampules are carried and are arranged as peas-in-a-pod with both ampules made of rigid thin impervious material such as glass and/or plastic. The inner ampule retains the concentrate, usually powder, and the outer ampule contains the fluid. A filter, such as stacked disks, is interposed between the distal end of the hollow needle and the ampules. The flexible cap end is manipulated to cause the two ampules to be broken after which the contained components are mixed by shaking and this mixture is drawn by aspiration through the filter into the syringe. The add-on device is then discarded and the now filled syringe is used in the conventional manner. Three variations of this device are shown with each arrangement providing the contemplated breaking availability and filtering capability.

15 Claims, 3 Drawing Figures

STORAGE, MIXING AND FILTERING RECEPTACLE FOR SYRINGE

BACKGROUND OF THE INVENTION

1. Field of the Invention

The field of this invention as established in and by the U.S. Patent and Trademark Office is believed to be found in the general class entitled, "Surgery" (Class 128) and in the subclass therein entitled, "Hypodermic" (Subclass 215) and in the subclass entitled, "mixing syringe" (Subclass 218M).

2. Description of the Prior Art

A pre-Ex search of the art was made and several U.S. and foreign patents or references were found. Among these patents are U.S. Pat. No. 2,769,444 to HENDERSON as issued on Nov. 6, 1956; U.S. Pat. No. 2,854,925 to CROCKFORD et al., as issued Oct. 7, 1958; U.S. Pat. No. 3,739,947 to BAUMANN et al., as issued June 19, 1973; U.S. Pat. No. 4,234,083 to COHEN as issued on Nov. 18, 1980 and U.S. Pat. No. 4,306,554 as issued to SCHWARTZ et al., on Dec. 22, 1981. Among the foreign patents are French No. 504,291 to CORBIERE as issued on June 29, 1920; Canadian No. 516,003 to PARRINE as issued Oct. 7, 1965 and Netherland Pat. No. 278,496 to BONNIN, S. A. as issued Nov. 10, 1964.

In these and other known devices the fluid is carried in one container and the powder is carried in a breakable ampule. Not shown in these references is Applicant's pea-in-a-pod concept in which both the fluid capsule and the powder capsule are rigid having thin shell portions that are broken to allow these components to be shaken to provide the desired mixture. The body of HENDERSON carries the fluid and acts as the syringe body. CROCKFORD uses a pin to puncture the small puncturable container which pin is also used to bring the fluid to the liquid drug. The fluid in BAUMANN is broken by a plunger with transference of the fluid to a powder. COHEN shows a rubber stopper that is displaced for intermixing and SCHWARTZ does not show fluid as carried in a capsule that is fractured before fracturing the powder containing ampule.

The foreign references also avoid the concept of a pea-in-a-pod. CORBIERE shows the powder capsule pierced by a pin or needle after which the mixed contents in a rigid container is withdrawn through a filter into a syringe. In PARRINE glass ampules have tip portions that are broken to allow the powder to be mixed with the fluid. It is to be noted in PARRINE that gas under pressure is used to expell the mixed components. In BONNIN it is shown that glass amplules are used, at least for the fluid, and in FIG. 2 for both fluid and powder. There is no suggestion of a fracture or breaking of both containers in a flexible outer cup end. The simple but effective device of Applicant provides for the use of a standard syringe and affixed needle. The to-be-mixed components are carried as an add-on and after mixing these components are drawn into the syringe through a filter with the add-on portion then discarded.

SUMMARY OF THE INVENTION

This invention may be summarized, at least in part, with reference to its object. It is an object of this invention to provide, and it does provide, an add-on storage sheath which is flexible and contains rigid frangible ampules or capsules arranged as peas-in-a-pod with the inner smaller ampule of glass containing the powder and with the outer larger ampule containing the fluid diluent. The flexible sheath is manipulated to cause the ampules to be broken after which the contents are shaken for mixing to the desired degree. This mixture is drawn through a provided filter into the interior of a syringe through the usual aspiration. The syringe is used in the usual manner after the add-on is removed and discarded.

In brief, there is shown and described in detail three embodiments of an add-on storage container for use with and on the barrel of a conventional syringe. A hollow needle is secured to the end of this syringe barrel in the usual manner and after securing the add-on is mounted for supplying a mixable medicament. A sheath, which is attached to the outer diameter of the barrel, includes a filter carried with and by this sheath portion. In one embodiment the filter is tubular and carries a cup deflector which is adapted to redirect the filtered and mixed fluid to the distal end of the hollow needle. A distal cup end of flexible, reasonably transparent plastic is secured to this sheath and is manipulated to break an outer rigid capsule of fluid and an inner rigid capsule or ampule of medicament. After breaking, the contents are shaken for mixing.

In an alternate embodiment the cup deflector is not used and the filter is a series of disks which are mounted in a sheath and spaced from the distal end of the hollow needle. Breaking of the pea-in-a-pod capsules exposes the components which are then mixed. Excess air in the distal cup member is partially removed by sliding the cup member up the sheath.

In a third embodiment the sheath member is made even longer with a central reduced portion conducive to bending if and as desired. The distal end of this sheath away from the barrel attached end of the syringe contains the filter disks. A flexible distal cup member is attached to this sheath member and encloses the rigid capsules of fluid and powder.

The embodiments contemplate that the flexible cup member is sufficiently transparent to enable the user to view the broken ampules and to mix the contents by shaking. The mixed fluid is then drawn through a filter means into the syringe. The sheath portion is also contemplated to be of sufficiently transparent material that drawing of the mixed fluid into the syringe is easily achieved. The add-on portion is removed from the barrel and discarded after the mixed fluid has been drawn into the syringe.

In addition to the above summary the following disclosure is detailed to insure adequacy and aid in understanding of the invention. This disclosure, however, is not intended to cover each new inventive concept no matter how it may later be disguised by variations in form or additions of further improvements. For this reason there has been chosen specific embodiments of a syringe with an add-on receptacle for storage, mixing and filtering of fluid and powder components as adopted for use for injecting medicaments and showing preferred means for assembly and use. These specific embodiments have been chosen for the purposes of illustration and description as shown in the accompanying drawing wherein:

BRIEF DESCRIPTION OF THE DRAWING

In the following description and in the claims various details are identified by specific names for convenience. These names are intended to be generic in their application. Corresponding reference characters refer to like members throughout the several figures of the drawings.

DETAILED DESCRIPTION OF EMBODIMENT OF FIG. 1

Figure 1:
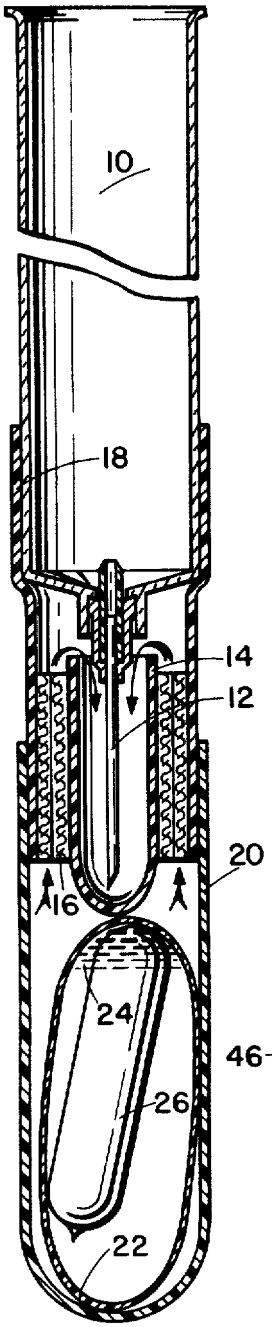
FIG. 1 represents a sectional side view, partly diagrammatic, and showing the detail of isolated and stored components that are broken and then intermixed and filtered as they are drawn into the syringe barrel.

Referring next to the drawing and FIG. 1, there is depicted a syringe barrel 10 or outer housing of a conventional syringe. This barrel is used with a plunger of known construction (not shown) and when drawn outwardly causes a negative pressure to be created in the barrel to draw fluid into said barrel. To a conventional syringe barrel a hollow needle 12 is affixed in a conventional secured manner. A cup deflector 14 provides a protective sheath for the secured needle. As shown, this cup deflector is retained in a spaced condition as shown by filter material 16. This material may be formed as a ring-like configuration or may be a series of disk-like components. The filter material is made or selected to provide the desired exclusion of unwanted particles.

The barrel 10 has a determined outer diameter and an outer sheath 18 is secured thereto in an airtight condition. This may be by a shrink fit or by an adhesive. This sheath is tubular in configuration and after positioning on the barrel 10 a distal cup end 20 is secured to said sheath. This cup end is mounted to the sheath so that there is provided an exclusionary and inhibitory seal of air and the like by the joint of sheath 18 and cup end 20.

A fluid ampule or capsule 22 is preferably made of very thin plastic or glass. A fluid 24 is shown in this ampule and is released when said ampule is broken. An inner medicament ampule or capsule 26 is usually of glass. Usually this contained component is a powder 28.

USE AND OPERATION OF EMBODIMENT OF FIG. 1

The syringe barrel 10 is a portion of a conventional syringe. To this barrel is mounted the filter and capsule container as depicted. The distal cup end 20 is made of flexible plastic and the user grasps and manipulates said cup end to cause the outer ampule 22 and the inner ampule 26 to be broken. The fluid 24 (diluent) is shaken with the now exposed powder (medicament) 28 until the desired mix has been achieved. This resulting mixture is drawn through the filter material 16 into cup deflector 14 and through the hollow needle 12 and into the interior of the barrel 10 in the normal aspirating manner. The outer sheath 18 and all associated components are removed from the syringe barrel 10 and discarded. Unwanted air in the barrel of the syringe is removed in the usual manner.

The fluid ampule or capsule 22 is shown as made of thin plastic. This is a preferred construction as it allows the fluid to be initially packaged at room temperature. The capsule may be formed into any desired configuration and fluid may be flowed into this container through a small hole which is closed by other plastic material. The new plastics now available are sufficiently brittle to enable fracture to be achieved while retaining properties for the retention of fluids such as water or like diluents. The movement of the mixture is indicated by the arrows from the distal cup 20 through the filter material 16 thence into the open end of the cup deflector 14.

EMBODIMENT OF FIG. 2

Figure 2:
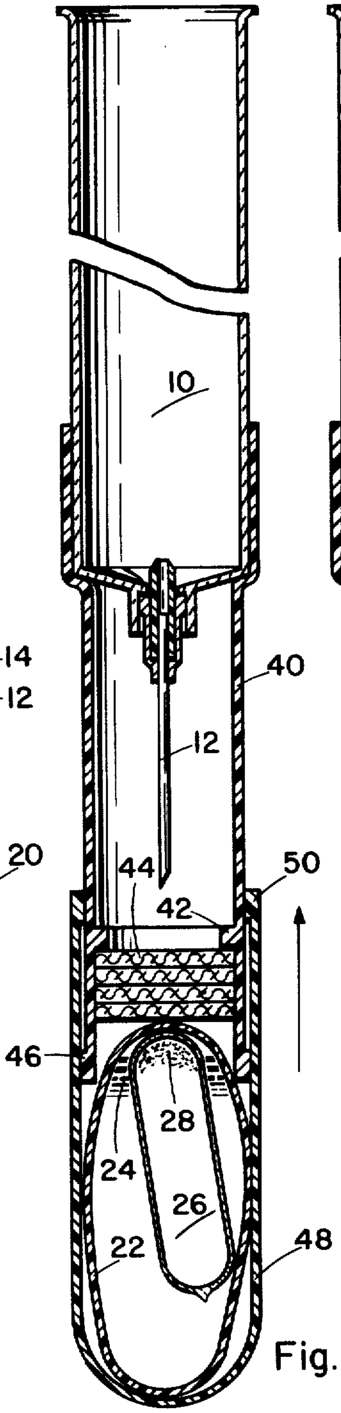
FIG. 2 represents a sectional side view, partly diagrammatic, and showing in detail an alternate embodiment of an isolation and storage of components before breaking, filtering and drawing the resultant mixture into the syringe barrel.

The apparatus shown in FIG. 2 is much like that of FIG. 1 above described but rather than a cup deflector 14 and ring-like filter 16 there is shown an alternate construction. To barrel 10 an outer sheath 40 is provided which is of an extent so that the tip end of secured needle 12 is not closed in any manner. This sheath 40 is formed with an inner positioning ring 42 which provides a stop for filter disks 44. These disks are a tight fit in this sheath. A wiper seal or ring 46 is provided on this sheath and extends outwardly and engages an inner diameter of distal cup member 48. This cup member, although made of flexible plastic, has an inwardly extending wiper seal or ring 50 which engages the outer diametrical surface of sheath 40. The fluid 24 is retained in ampule or capsule 22 and the powder is contained in the ampule 26 as in FIG. 1.

USE AND OPERATION OF EMBODIMENT OF FIG. 2

The operation of this embodiment is very like that of FIG. 1 in that the ampules 22 and 26 are broken by the user or operator as the cup member 48 is caused to move inwardly. After breaking, the diluent and powder are shaken until the desired mix has been achieved. Aspiration of the syringe now draws the mixed fluid into the syringe and through the filter disks 44. Unwanted air is expelled in the conventional manner.

The arrow to the right of the filter disks 44 indicates that after breaking the capsules 22 and 26 and shaking for mixing, a portion of this space in the distal cup 48 may be lessened by and with a sliding of cup 48 along sheath 40 until the residue from the ampules reaches the filter disks 44.

EMBODIMENT OF FIG. 3

Figure 3:
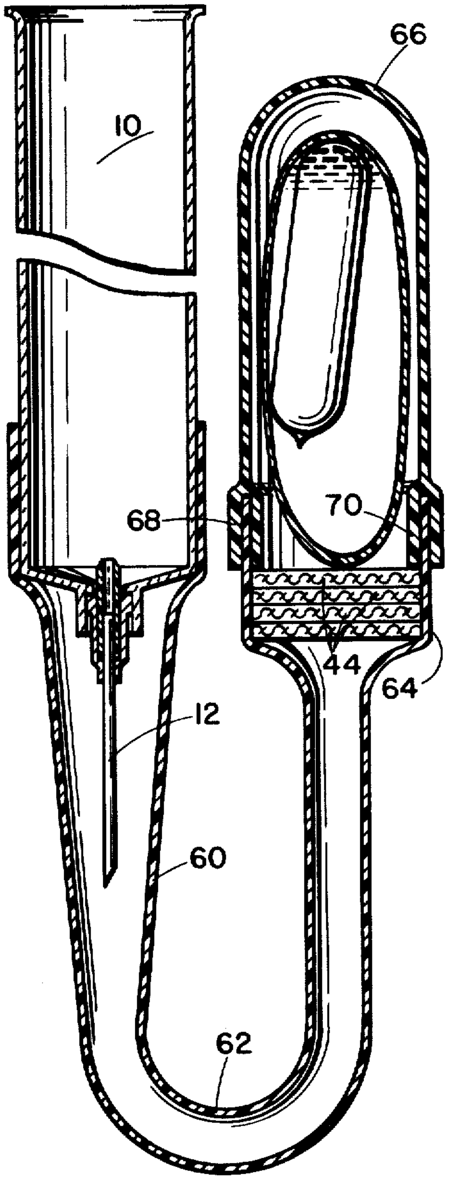
FIG. 3 represents a sectional side view, partly diagrammatic, and showing in detail yet another alternate embodiment of an isolation and storage of components before breaking, filtering and drawing into the syringe barrel.

Referring next and finally to the embodiment shown in FIG. 3, it is to be noted that instead of a sheath of a length substantially that of the needle 12 the tubular connection may be of a greater length. To the syringe barrel 10 is mounted a tubular and flexible member 60 which at one end engages and mounts on the outer diameter of the barrel 10. This tubular member as depicted has a reduced central portion 62 that may be bent as desired. The other end of this member is expanded at 64 to provide a seating recess for disk-type filters 44 like or similar to that used in the embodiment of FIG. 2. A distal cup member 66 is secured to the expanded end 64. Sealing means such as an outer ring-like coupling and a seating stop 68 are shown but other means for making an airtight seal may be provided. Sealing means may include sonic welding or chemical welding of cup 66 to expanded end 64. What is desired is that the interior of the cup member 66 be inviolate during manipulation and fracture of the ampules.

USE AND OPERATION OF EMBODIMENT OF FIG. 3

As in the other embodiments, the ampules or capsules 22 and 26 are broken when the cup member 66 is caused to be deflected from its as-molded condition. The broken ampules or capsules permit the diluent and powder to be shaken and mixed. The filter 44 prevents unwanted particles from entering the needle 12 and aspiration of the syringe is in the usual manner.

It is to be noted that in the manufacturing process the inner ampule 26 is usually made of glass and in drawing a small opening at one end is provided. Through this opening the powder is supplied and this ampule is then closed by heating with a small tip being the usual result.

In the three embodiments above described it is anticipated that the ampules or capsules 22 and 26 are easily broken by manipulation or squeezing of the end plastic coverings. The ampule carrying the powder is usually of glass with the end or opening sealed by heat. This may leave a small protrusion but the intermediate portion is easily fractured. The shape is shown as oblong but any shape may be provided. The fluid container is also shown as oblong or an ellipsoid, but the shape is made to suit particular conditions and the shape is not a condition for use. The outer container is contemplated to be of plastic of a thin wall. This plastic is very resistant to the transfer of fluids and is quite frangible. Whether made with a small aperture and closing this aperture with other plastic means or forming the ampule 22 as telescoping portions and sonic or chemical welding is merely a matter of preference.

The distal cup or end portion is made of flexible plastic enabling both contained capsules or ampules to be fractured. The ampule 26 is shown within ampule or capsule 22 to provide a reduced overall length and also to insure that the outer ampule is broken before and with the inner ampule or capsule. In a side-by-side arrangement this is not guaranteed. During shipping the fluid carried by the ampule or capsule 22 provides a small cushion or shock absorber for the interior ampule 26. The cup end portion holding these ampules is sufficiently transparent to enable the user to view the breaking and mixing of the ampules 22 and 26 then the aspiration of the syringe to draw the mixed components through the filter and into the syringe.

The inner ampule 26 is conventionally of glass and the contents are usually a powder but this does not preclude anticipating a paste or liquid that is to be mixed with a diluent just before injection. If and when storage in a glass ampule is difficult the use of one of the new plastics that may be sealed by chemicals or sonic welding is contemplated. The new plastics with sonic and laser joining are constantly being invented and promoted. Thus, the composition of the outer container is a matter of economics and preferred construction at the time of manufacture. The sheath and distal cup end is contemplated to be a molding of plastic and flexibility and transparency is desirable. The effectiveness of the filter is determined by the contents being mixed since many filters are now effective in excluding particles no larger than one or two microns in size. The determining factor in selecting a filter is the anticipated use.

The sheath and distal cap end may be made as one molding with an open end for inserting the two ampules or capsules. The filter is inserted and positioned before inserting the ampules and then the distal end is closed by heat sealing or the like. As and since the cap end is flexible and reasonably transparent the closure may be with a heat seal and then trimmed but any exclusionary seal is contemplated. The retention of the filter and the sheath on the barrel of the syringe is also a matter of design as to the end use of the product.

As shown, the ampules or capsules have frangible thin sidewall portions employing an end closure but this does not preclude the making of said ampules as telescoping or with a lap fit that may utilize welding, cement or a press and interference fit. After securing together, the side walls are easily fractured to expose the interior contents. Usually the sidewalls are only a few thousandths of an inch in thickness and are broken by and with a small application of force. The interior ampule or capsule usually contains a powder but a paste or fluid is not excluded since a separation of the contents of the ampules is maintained until just before use.

The use of polyethylene and like plastics for the rigid outer ampule anticipates that the wall thickness is sufficient to enable a fracture to occur. When and where polyethylene is used a wall thickness of about six to eight thousandths of an inch is contemplated. For long periods of storage the resulting outer container, after sealing, may be coated with a silicone liquid and/or the like producing or providing a very thin retaining film. Sonic welding of thin walls may require as little as two or three tenths of a second and with substantially very little or no heat. Boiling or vaporizing of the contained fluid is thus avoided and changes in properties do not occur. The outer sheath being very flexible is preferably made of polypropylene, but other plastics having similar properties may be provided. Prototype models to prove the principals disclosed may not be the best mode for production but a "best mode" will be tailored to the product to be packaged. Usually the inner ampule is of glass and with a size less than a cubic centimeter. The fluid in the outer ampule is usually three to five cubic centimeters. The outer ampule is contemplated to be produced in production with a molded shape.

Although sheath 18, 40 and 60 are shown slidably secured to the barrel 10 of the syringe, this does not preclude the forming of the sheath so as to be secured to a reduced diameter hub of the barrel in which the needle 12 is mounted. As this hub portion is usually small in diameter and extent, gripping wing portions may be provided on the sheath. It is contemplated that the sheath may be attached to a second protective sheath or conduit removably attached to the syringe barrel or hub and providing therewith exclusion and/or protection from contamination. This interior sheath may be just slightly larger than the needle and in the attached condition provide a reservoir for the mixed fluid. The deflector cup 14 of FIG. 1 may be provided with securing assists such as barbs, adhesive and/or outwardly projecting rib portions. The filter as used in all embodiments is adapted to be placed so that all mixed fluid must pass through the filter and into the needle. Additional protective means for the filter such as a metal or plastic screen may be provided to insure that broken glass or plastic particles do not damage the filter capability. Although one filter assembly is shown this does not preclude plural filters.

Terms such as "up", "down", "bottom", "top", "front", "back", "in", "out" and the like are applicable to the embodiments shown and described in conjunction with the drawing. These terms are merely for the purposes of description and do not necessarily apply to the position in which the storage, mixing and filtering receptacle for syringe may be constructed or used.

While particular embodiments of the add-on storage, mixing and filter apparatus have been shown and described it is to be understood the invention is not limited thereto and protection is sought to the broadest extent the prior art allows.

What is claimed is:

1. An add-on device for storing, mixing and filtering a fluid and concentrated component, said add-on device including:

(a) a syringe having a rigid outer barrel;

(b) a hollow needle secured to a distal end of said outer barrel and providing a communication pathway from the exterior to the interior of said syringe barrel;

(c) a tubular sheath having two ends with a first end of said sheath mountable in a fluid-tight manner on the outer surface of the distal end of said barrel or an interior sheath member removably attached to said end, said tubular sheath having an extending portion in and on which the secured end is formed;

(d) means for closing the second end of the sheath and inhibiting the passage of any air and the like into the sheath after mounting said sheath on the barrel and closing of the second end;

(e) a rigid inner ampule or capsule with a thin wall susceptible for breaking and in a stored condition encapsulating a concentrate, after which it is sealed to prevent loss of contents;

(f) a rigid outer ampule or capsule with a thin wall adapted for breaking and in a stored condition having fluid and said inner sealed ampule therein and then said outer ampule is sealed to prevent loss of stored contents, and (g) filter means interposed between the distal end of the hollow needle and the sealed rigid outer ampule, said filter means mounted in the sheath so that any and all released and mixed fluids must and do pass through the filter means by negative pressure developed through aspiration of the syringe whereby that sheath portion near the closure end and adjacent the rigid outer and inner ampules is sufficiently flexible and thick so that manipulation by an operator of said flexible portion may be made to break said ampules, shake the now exposed contents and draw this mixture through the filter means and into the syringe after which the add-on device is removed from the syringe barrel and discarded.

2. An add-on device as in claim 1 in which the filter means is a tubular configuration and is secured in the sheath and that center portion interior of the tubular filter means is a cup-shaped deflector that is retained by said tubular filter means and this deflector surrounds the tip end of the needle to provide a flow path thereto and with the open end of the cup-shaped deflector open to the fluid mix after shaking and passing through the tubular filter means.

3. An add-on device as in claim 2 in which the rigid inner and outer ampules are carried in a flexible distal cup end which is secured to the tubular sheath and provides the closure end seal of said second end.

4. An add-on device as in claim 3 in which the distal cap and the tubular sheath are generally circular and have a telescoping fit of one to another.

5. An add-on device as in claim 4 in which the filter means is carried in the tubular sheath.

6. An add-on device as in claim 5 in which the filter means is fixedly secured to both the sheath at or near the second end thereof and the cup-shaped deflector is fixedly secured to the tubular filter.

7. An add-on device as in claim 1 in which the securing of the sheath is on the larger diameter of the barrel.

8. An add-on device as in claim 1 in which the filter means is disk-like in configuration and the filter means is positioned in said tubular sheath so as to prevent any flow toward the syringe other than through the filter means and with this position said disk-like filter means is spaced from the distal end of the needle.

9. An add-on device as in claim 8 in which the filter means is a plurality of disks and a stop means is provided in the sheath so as to limit the inward placement of the filter means.

10. An add-on device as in claim 9 in which the inner and outer rigid ampules are carried in a distal cap end which provides the closure and seal of said second end.

11. An add-on device as in claim 10 in which the sheath is formed with an outwardly directed seal ring and the open end of distal cap end is formed with an inwardly directed seal ring, the seal ring diameters establishing a sliding exclusion of unwanted external air while establishing an outer limit of movement of cap to sheath and after the ampules have been broken in the distal cap end, this cap end and these broken portions are brought adjacent to the positioned filter means.

12. An add-on device as in claim 1 in which the tubular sheath is of elongated configuration and flexible and with the distal second end formed to receive and retain said filter means.

13. An add-on device as in claim 12 in which the filter means is a plurality of disks and the enclosing of the inner and outer ampules is a flexible cap end.

14. An add-on device as in claim 13 in which the second end of the sheath and the open end of the flexible cap end are joined together with a tongue and groove arrangement.

15. An add-on device as in claim 1 in which the tubular sheath is secured to the syringe rigid barrel and provides retention means for the filter means.

* * * * *